United States Patent
Correges

[11] Patent Number: 6,130,056
[45] Date of Patent: *Oct. 10, 2000

[54] DEVICE FOR THE STUDY OF ORGANOTYPIC CULTURES AND ITS USES IN ELECTROPHYSIOLOGY AND BIOCHEMISTRY

[75] Inventor: Philippe Correges, Lugrin, France

[73] Assignee: Chemodyne S.A., Switzerland

[*] Notice: This patent is subject to a terminal disclaimer.

[21] Appl. No.: 09/040,211

[22] Filed: Mar. 17, 1998

Related U.S. Application Data

[63] Continuation-in-part of application No. 08/765,043, filed as application No. PCT/IB96/00300, Apr. 10, 1996, Pat. No. 5,759,846.

[30] Foreign Application Priority Data

Apr. 12, 1995 [FR] France .................................. 95 04410

[51] Int. Cl.[7] .............................. C12Q 1/02; C12M 3/00; C12M 1/34; G01N 27/00
[52] U.S. Cl. .................... 435/29; 435/284.1; 435/287.1; 435/288.3; 435/297.2; 422/82.01; 422/104
[58] Field of Search ................................ 422/82.01, 104; 435/29, 284.1, 287.1, 288.3, 297.2

[56] References Cited

U.S. PATENT DOCUMENTS

| | | | |
|---|---|---|---|
| 4,889,691 | 12/1989 | Argentieri | 422/102 |
| 5,064,618 | 11/1991 | Baker et al. | 422/82.01 |
| 5,126,034 | 6/1992 | Carter et al. | 204/403 |
| 5,759,846 | 6/1998 | Stoppini et al. | 435/284.1 |

FOREIGN PATENT DOCUMENTS 0 609 458  8/1994  European Pat. Off. .

OTHER PUBLICATIONS

Keese et al., IEEE Eng. Med. Biol. 13(3), 402–408, 1994.

*Primary Examiner*—Kenneth R. Horlick
*Attorney, Agent, or Firm*—Bierman, Muserlian and Lucas

[57] ABSTRACT

In a device for studying and recording electrophysiological phenomena in culture of excitable tissues comprising a lower half card with a perfusion membrane in a perfusion chamber sealed by a permeable and transparent membrane and an upper half card with a flexible printed circuit bearing a network of electrode and fitted with a cap for insuring the closure of the device, the improvement comprising the upper half card being comprised of an upper half and a lower half card which when assembled together for recording yield a functional set up.

7 Claims, 15 Drawing Sheets

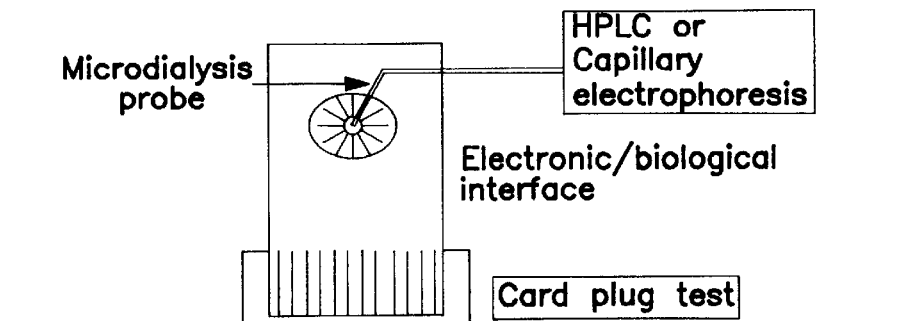
FIG. IA
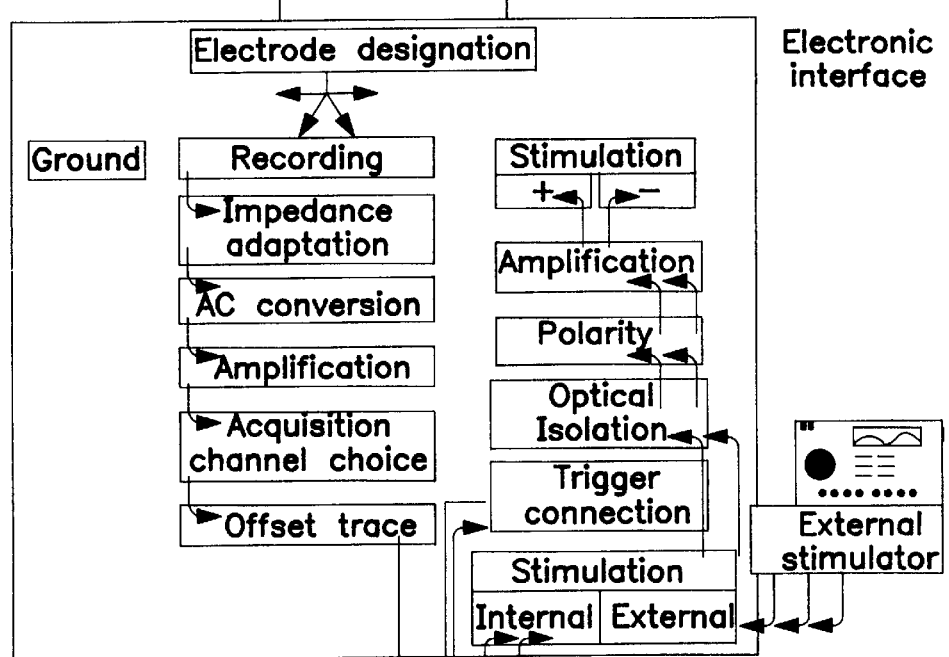
FIG. IB
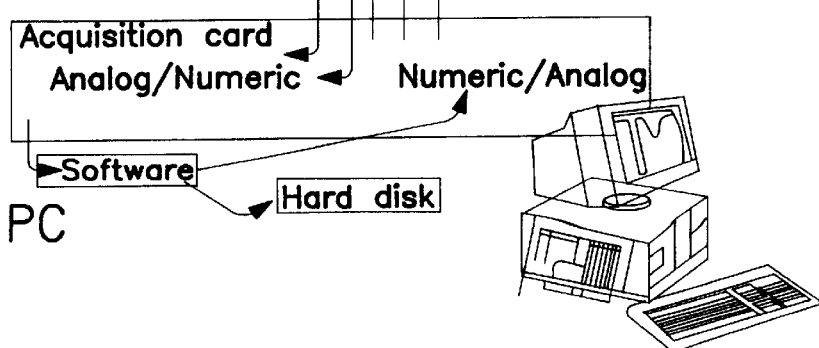
FIG. IC

7mm

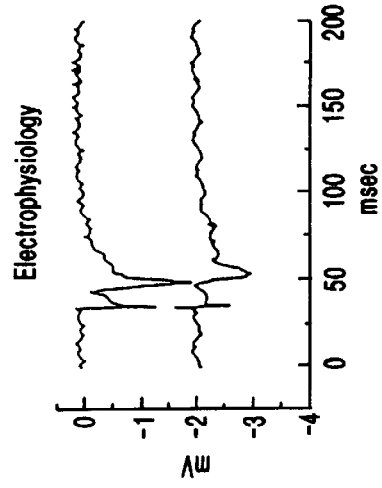
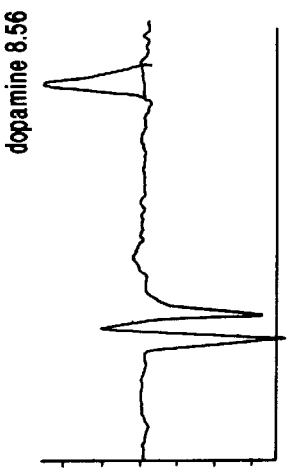
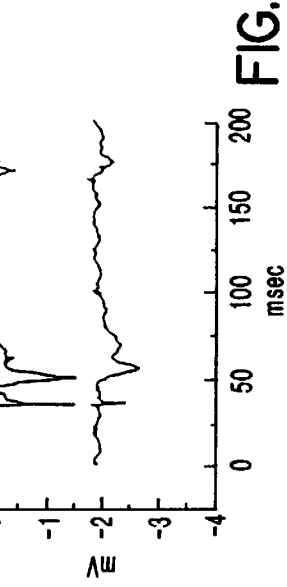
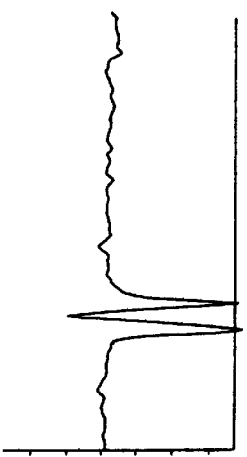
FIG. 9A — HPLC (Microdialysis)
FIG. 9B — Electrophysiology and Control
FIG. 9C — dopamine 8.56
FIG. 9D — Dopamine Perfusion
FIG. 9E
FIG. 9F — Wash

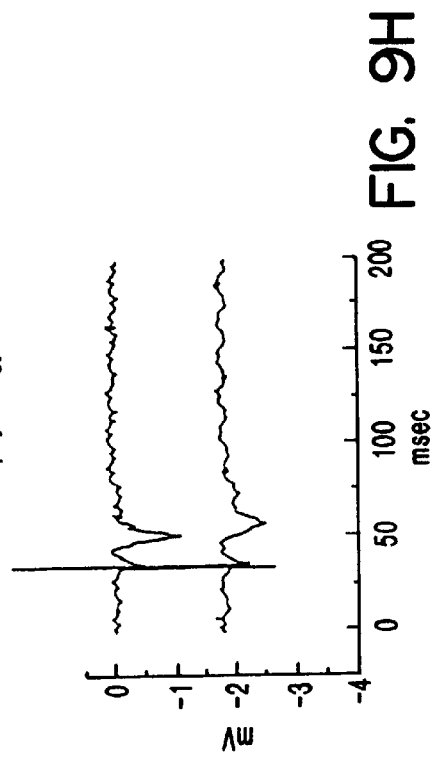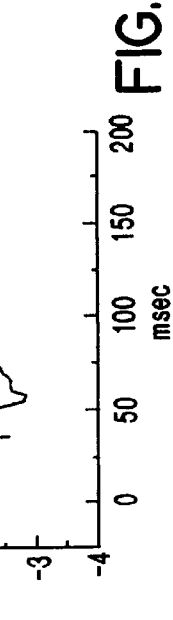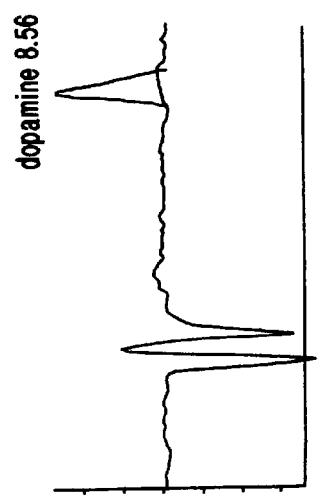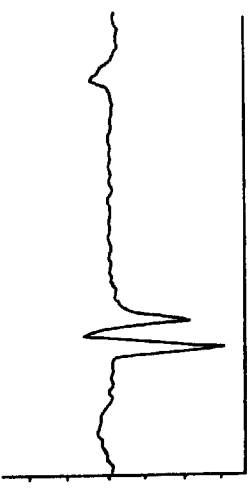

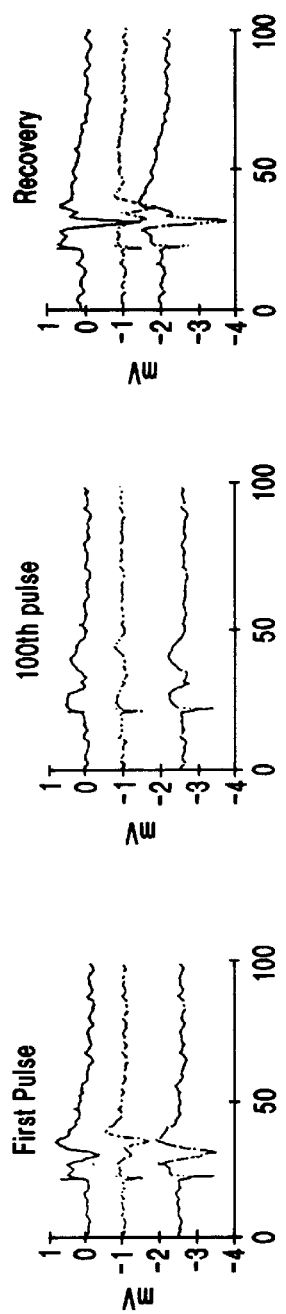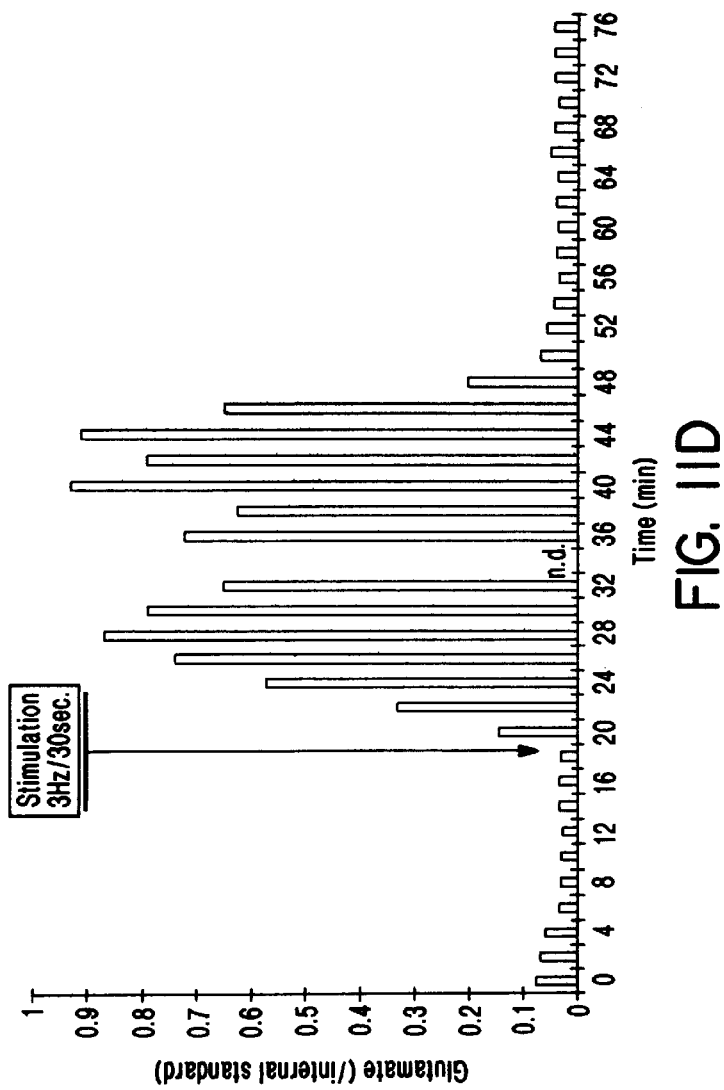

DEVICE FOR THE STUDY OF ORGANOTYPIC CULTURES AND ITS USES IN ELECTROPHYSIOLOGY AND BIOCHEMISTRY

The present application is a continuation-in-part of U.S. patent application Ser. No. 765,043, filed Dec. 10, 1996, now U.S. Pat. No. 5,759,846 which is a 371 application of PCT/IB96/00300 filed Apr. 10, 1996.

SUMMARY

The present invention relates to the domain of electrophysiology and biochemistry and to the measuring devices in these domains.

The present invention relates to a new device which enables tissular explants or organotypic cultures to be kept alive, allowing the electrophysiological and biochemical activity of the tissue studied to be continuously measured and analyzed.

The invention relates more particularly to the manufacture of an interface between the biological tissue and a suitable electronic module. The complete system allows the study of the electrical phenomena which are produced in excitable tissue cultures and in particular in central nervous tissues during the culture, the regeneration or the differentiation of cells.

Subject matter of the biological/electronic interface is a study device. It is constituted by two half-cards forming the upper part and the lower part respectively of the interface.

A permeable and transparent membrane is fixed on to the lower part of the device. One or several slice cultures rest on it which can be continuously or discontinuously perfused with a liquid nutrient.

PRIOR ART

Various extracellular recordings of the electrophysiological activity have been previously performed using micro electrode arrays. Most of the technologies used were microphotolithography on different types of material, like silicon (Kovacs et al., 1992; Curtis et al., 1992), glass (Thomas et al., 1972; Pine et al., 1980; Novak et al., 1988, Gross et al., 1982 & 1993). From these micro electrode arrays, simultaneous stimulations and recording of neuronal activity were performed on monolayer networks (Gross et al., 1993). So far, the longest recording periods on nervous slices did not exceed 14 hours. In order to improve the survival conditions of the tissue, perforation of the stand was performed by some authors (Boppart et al., 1992).

Usually two methods were used. The first, is an exterior stimulation and recording by the micro electrode array; the second, is a stimulation by the network and recording by a conventional glass micro pipette. All those systems involved a recording chamber placed in a Faraday cage and most of them needed a classical electrophysiological set-up (antivibration table, head stage, amplifier, stimulation unit, isolation unit, oscilloscope, micro manipulator, . . . ). In most cases the biological material used were dissociated neurones or acute slices. Cells or tissue were laid down onto a planar electrode array and most of the time, glia cells were in between neurones and the recording site impeding correct recordings (Janossy et al., 1990).

So far, no available system provides the possibility to simultaneously stimulate and get multirecordings of electrophysiological activity on organotypic slice cultures from mammals central nervous system (CNS), outside a Faraday cage during several days.

This prior art may be well illustrated by the following references

Wade G. Regher and al.—J. of Neuroscience Methods 30 (1989) p. 91–106
J. Pine—J. of Neuroscience Methods 2 (1980) p. 19–31
S. Martini and al.—J. of Neuroscience Methods 48 (1993) p. 115–121
J. L Novak and B-C Wheeler—J. Neuroscience Methods 23 (1988) p. 149–159
S. A Boppart—IEEE Transactions on Biomedical Engineering 39 (1992) p 37–41
E. Hoffer and al.—Am. J. Physiol. 266 (1994) p. H2136–H2145
P. Connolly and al.—Biosensors and Bioelectronics 5 (1990) p. 223–234
G. W Gross and al.—J. of Neuroscience Methods 50 (1993) p. 131–143
P. Fromherz and al.—Science 252 (1991) p. 1290–1293
D. S Barth and al.—Brain Research 678 (1995) p. 177–190
V. Janossy and al.—Acta Biologica Hungarica 41 (1990) p. 309–320
A. S. G Curtis and al.—Med. and Biol. Eng. and Comput, 30 (1992) CE 33–36
G. T. A Kovacs and al.—IEEE Transactions on biomedical Engineering 39 (9) (1992) p.893–902
C. A Thomas and al.—Exptl. Cell Res. 74 (1972) p.61–66

Most of these references relate to micro-electrode array, using microphotolithography technology.

The two following references may also be cited:

Ch. Reese and I. Giaever IEEE Engineering in Medicine and Biology 13 (1994) n°3 p.402–408 who describe biosensors made of a small gold electrode immersed in a cell culture medium. This sensor is devised to detect changing impedance consecutive to the attachment of the cells and their growth on the gold electrode, but does not allow the recording of activity of excitable cells.

P. Arquint and al. (Clinical Chemistry 40—1994—p. 1895-1809) disclose a silicon chip micromachined analyser. This system uses silicium technology to produce a pH and $CO_2$ detector in biological fluids, but is not appropriate for the cell culture. This device is made to be implanted and not to study the survival or the growth of slices of culture tissue.

None of these systems allows the study of electrophysiological activity of nervous tissue slices. They cannot deliver any electrical stimulation nor collect the electrophysiological responses, evoked or spontaneous, coming from the nervous system.

DISCLOSURE OF THE PRESENT INVENTION

The present invention was made to remedy the above-mentioned limitations. It is an object of the present invention to permit the long term survival of mammals CNS slice cultures in order to study electrophysiological activity and biochemical analysis of cerebral parenchyma. Organotypic slice cultures keep the tissue organization similar to the in-vivo one.

The three dimensional organization of the tissue allows to gain a current density higher than the one which can be recorded with the dissociated culture cells. Detection of synaptic responses can thus be more easily realized by extracellular recording electrodes. In addition, this kind of tissue culture allows longer recording time compared to acute slices studies. This enables to study long-term phenomena, like delayed neuronal death, neurotoxicity or neurodegenerative processes.

With this system one can perform continuous and simultaneous stimulation and recording of neuronal activity during several days. Microdialysis technique was adapted to the electronic/biological interface according to the invention, in order to collect biochemical molecules from the extracellular medium or to deliver chemical molecules into the cerebral parenchyma.

PREFERRED EMBODIMENTS OF THIS INVENTION

The device includes two half-cards which fit together to form one card which can be inserted into an electronic module specially designed for this purpose.

This card can be perfused in a sterile manner either with a control culture medium, or with a selected culture medium containing the substances which one desires to test or the mediators the effects of which on the preparation, one desires to determine. The composition of the culture medium is defined more precisely in the experimental part.

A method described by L. Stoppini (journal of Neuroscience Methods 37 (1991) p.173) was already known, in which slices of nervous tissue from rat hippocampus were kept under culture at the interface between the air and a culture medium. The slices, placed on a sterile, transparent and porous membrane, were kept in a Petri dish placed in an incubator. Histological and electrophysiological studies made it possible to show that this technique allowed explants to be kept alive and a tissular organization close to that which can be found <<in vivo>>, to be retained.

The aim of the present invention is to enable organotypic cultures to survive outside an incubator and a Faraday cage and to be able to carry out, on these cultures, continuous electrical stimulations and electrophysiological recordings, over several days up to several weeks.

For this purpose, the device according to the invention allows a network of biocompatible electrodes (plated gold 24 carats) to be put in contact with the surface or with the inside of the tissue studied.

The lower part of the card is made of plastic material and comprises a cavity having an inlet and an outlet. The cavity is delimited by a permeable and transparent membrane. Tissue slices (200–400 µm) produced by a chopper or a Vibratome is placed on the membrane. The culture medium passes through the membrane by capillarity and covers the tissue with a film of liquid. This arrangement is effective for ensuring a good survival of the cells for several weeks by supplying the necessary nutriments and facilitating the diffusion of oxygen and carbon dioxide throughout the tissue slices.

The inlet and the outlet for the liquids of the lower part of the card can be sealed by a septum of medical quality, thus forming a lock which enables the contained liquids of the lower chamber, to be preserved. It can then be conveniently replaced in one run or continuously, in a sterile manner, without having to proceed with this operation under a sterile atmosphere or under laminar flow.

The upper part of the card is fixed, using clips, or screw systems to the lower part. The upper part of the card is composed of an element made of plastic material and a flexible printed circuit which forms a network of electrodes attached to connectors.

The plastic element has a well containing a moveable sleeve which can progressively move downwards when a cap is screwed on the well. The downwards progression of the sleeve, by pressing on the flexible printed circuit, allows the electrodes to be vertically positioned on the surface of or inside the slice. By this process, there is no twisting movement exerted on the flexible printed circuit and in this way one avoids damaging the biological tissue.

The presence of a flexible or rigid seal between the two half-cards ensures the impermeability of the gaseous chamber of the upper half-card of the device. This chamber is continuously humidified by evaporation through the membrane of the medium contained in the cavity provided to contain the liquid of the lower half-card. When necessary, a damp filter paper can also be added to a portion of the sleeve.

Observation of the tissue can take place by visual examination, by transparency, both of the upper side and the lower side of the card.

The tissular explants which are placed in the device can be kept alive up to several weeks outside an incubator and are thus monitored, at the same time, by visual supervision and by electrophysiological monitoring.

The tissular explants can be cultured either directly in the card, or can initially be cultivated in an incubator on membrane discs, placed in Petri dishes. The slices of tissue cultivated on the membrane pastilles can then be placed on the membrane of the card. The tissular explants can survive in this way in spite of the overlapping of two membrane layers.

The survival of the tissues studied was revealed by labeling using vital stains on the living tissue and by histological studies under light-optical, electron microscopy and by immuno-histochemical studies, after fixation of the tissues.

The survival of the tissues studied was in particular revealed after labeling with vital stains and by measuring the lactate dehydrogenase (LDH) content in the culture medium. In addition, immuno-histochemistry provides information about the return to operation of the neurons and of glial cells, bringing about the labeling of the neurofilaments for the neurons and the labeling of the <<glial fibrillary acidic protein>> (GFAP) for the glial cells.

The electrophysiological recordings allow the immediate determination, as a function of the responses obtained, of the physiological condition of the excitable tissue studied.

Measurement of the activity of the tissue comprises the recording, digitalization and measurement of the spontaneous electrophysiological responses and of the evoked responses.

ELECTRONIC MODULE

The electronic module is composed as follows:
the biological/electronic interface card plugs into an electronic module the functions of which are the following:
Each electrode of the interface can be dedicated either to positive stimulation (Stim+) or to negative stimulation (Stim−)
to recording (Rec.)
to earth (ground)
Description of these three functions:
Stimulation
Stim+, Stim−: the order for stimulation and triggering is given either by the computer, or by an external stimulator. All the stimulation electrodes are electrically isolated by optocoupling. They also have a variable gain and can be permuted.
Recording
After adjustment of the impedance, conversion to AC, amplification by a convenient factor (e.g 100, 500), and an adjustable offset, the choice of acquisition channels for the analogue/digital conversion card is possible.

Grounding

To avoid a phenomenon of antenna, the non-utilized electrodes are put at the reference potential.

The reference electrode is made by gold deposition around the lower chamber. This electrode is in close contact with the culture medium when it is injected in the lower part chamber. When the two half cards are adjusted, this reference electrode is automatically connected to the electronic ground. A test for good positioning of the card is visualized through a lightened diode.

Microdialysis Analyses

To show the use of the device according to the invention, details will be given hereafter on the biochemical measurements and the adaptation of the microdialysis technique to the device according to the invention.

Alongside the measurement of the electrophysiological activity, biochemical analyses of the extra-cellular medium can be carried out continuously using one or more microdialysis probes.

The microdialysis probe can be positioned at the level of the membrane situated on the lower part of the card, after what the tissue is placed on or under the probe. Another possibility is to fix the probe on the printed circuit. In this case, the vertical positioning of the probe, relative to the tissue, is carried out in the same way as for the electrodes.

The probe is continuously perfused by means of a syringe fitted with an automatic progression piston.

The dialysate collected from the probe is subjected to an analysis either by HPLC with automatic injection using an electrical 6-port valve, by capillary electrophoresis or by radioimmunoassays.

The microdialysis probe also allows one or more molecules to be delivered directly into the parenchyma of the tissue and in this way allows the chemical or physiological changes brought about by these substances to be analyzed.

It is another subject of this invention that is an improved embodiement of the device for maintaining tissue explants in a viable state and performing underside electrophysiological recordings. This embodiement features an original electrode network to achieve this result. Better quality electrophysiological recordings, simplified experimental procedure and absence of tissue damages are among the main benefits provided by this improvement, in particular for time extended experiments.

Accordingly, the modular construction blocks used for implementing the improvement in the underside recording chamber are the same as those for the upperside previous recording technique and require only minor modifications. In order to avoid any potential lesion due to the positioning of the electrodes on the tissue under study, it has been realized a recording system that complements the one previously described wherein the tissue is laid flatwise on a microelectrode network. In typical electrophysiological systems, the electrodes are made of borosilicate, in the present system, recording is carried out by a compatible gold-plated free-end electrode network for the upperside format and a compatible gold-plated fixed-end electrode network for the underside format. By such two variants of the system, as compared to all those previously described, continuous or discontinuous infusion of the investigated tissue can be performed. By this means, it is therefore possible to evaluate electrophysiological response changes following addition to the infusion medium, of a molecule of known or unknown activity. This medium can be either a predefined culture medium appropriate to the tissue being studied, or an electrophysiological fluid. The mechanical strength of the fixed-end electrode network makes it suitable for repeated use. By virtue of this modular system, one can effect upperside as well as underside electrical activity recordings, with only few minor changes being required.

The main advantage of underside recording derives from the fact that no damage would be caused to tissue by the positioning of the electrodes on the tissue surface and the point that the electrodes are much smaller than those employed in the upwards electrode network format. The biological/electronic interface of the underside version uses the same two plastic half-cards as the upperside version, except that two lower half-cards and one upper half-card are required. The position of the lower half-cards is unchanged while the upper part is inverted and fixed by means of four screws to the lower part. The fluid intake and exit ports in the lower portion of the board are each plugged up by a medical grade Luer adaptor. Tight closure between the two split-boards is ensured by two gaskets. This assembly features one 2 ml capacity infusion chamber. One transparent permeable membrane is disposed on the infusion chamber. An electrode network is then fixed on the infusion chamber. In this network, a number of holes have been bored so that the tissue slice can be supplied with nutrient fluid containing essential elements for survival. In addition, these holes allow visual inspection of the tissue and arrangement thereof over the network. This network contains 30 electrodes which can serve as recording or stimulatory units. Active portions, i.e. which are electrically conductive, are of rectangular-shape measuring 50 $\mu$m×100 $\mu$m. Recording portions are minute and this results in enhanced accuracy of the system, the number of neurons monitored by a given electrode being small. The tissue slice (200–400 $\mu$m) cut with a chopper or vibrating blade, is disposed on an eyelet that has been drilled inside a hydrophilic Teflon® membrane during the cultivation procedure. The Teflon® eyelet bearing the culture is laid on the active portions of the electrode network. The remaining lower half-card is inverted and laid over the lower assembly to form the gas exchange chamber which is plugged up by 2 Luer systems provided with filters (0,45 $\mu$m-porosity). The presence of a flexible or rigid gasket between the lower assembly and the upper half-card insures tight closure of the gas chamber in the device upper half-card. The lower assembly and the two upper half-cards are mounted by means of two screws thus forming a card which can be inserted into the electronic housing designed to accommodate for this purpose. All parts can withstand sterilization treatment (70% alcohol and UV rays) which is indeed a marked advantage in long range experiments. The signal to noise ratio of electrophysiological signals is excellent as demonstrated by underside elicited electric potentials in FIG. 3. Activity recording is neither hindered nor distorted by the presence of a hydrophilic Teflon ® membrane acting as a culture substrate. Direct positioning of the tissue on the electrode network is simplified thus allowing direct visualization. Positioning of the microdialysis probe is facilitated in as much. When placed inside an incubator, this arrangement can be tested once assembled, without requiring direct tissue manipulation. It's use is recommended in extended long range applications. Through electrophysiological recordings, it can be determined instantly, depending on the quality of responses obtained, the physiological state of the excitable tissue under study. Measuring the tissue activity involves recording, digitizing and measuring spontaneous and elicited electrophysiological responses.

Start-up of this underside monitoring system is a bit longer but, in the present procedure, the problem is viewed from a different angle so that different issues are being investigated.

It is therefore observed that the device according to the invention has the following advantages, relative to the existing devices for <<in vivo>> and <<in vitro>> studies:

- simplification and time saving with regard to changing the medium
- maintaining the concentration during the perfusion of molecules tested
- lack of obligation to place the tissue cultures in an incubator
- possibility of observing the development of the cultures for several days under a microscope or by means of a video camera
- saving of space and economy of material
- disposable analysis cards, which can be industrially produced in large amounts (Mass production)
- absence of the risk of residual mixing of the molecules tested
- possibility of using the device for cultures of dissociated cells or for studying <<freshly dissected>> tissue section
- reduced risk of contamination
- continuous (chronic) stimulation and recording, for several days to several weeks, of the electrical activity of the tissue studied
- the culture can be studied either continuously during several days or discontinuously from time to time, when put back into the incubator in between two recording periods.

Further it can be seen that the improved embodiment according to the invention offers the following advantages, in comparison to currently known <<in vitro>> experimental multiple recording devices:

- less bench space is required and the equipment is simplified
- contamination is minimized
- long range continuous or discontinuous stimulation and recording of electrical activity of the tissue being studied are feasable, without fear of mechanical lesions.

These two embodiements (upperside and underside recording) complement each other and are based on the same technical features.

Other advantages, goals and characteristics of the present invention will become more apparent from the description that follows in regards to the appended drawings wherein

BRIEF DESCRIPTION OF THE DRAWINGS

FIG. 1 is a schematic diagram of the system.

FIGS. 9A to J are graphs of simultaneous recording of electrophysiological activity (on the left) and biochemical analysis (in the right).

FIGS 11A to C are simultaneous recordings of electrophysiological activity and biochemical analysis with the apparatus of FIG. 10 and FIG. 11D in a graph thereof.

The schematic diagram of the system assembly is represented in FIG. 1.

This is composed of three main parts:

A. the biological/electronic interface

B. the electronic module specially designed to receive the interface to stimulate and to amplify the responses originating from the network of electrodes in contact with the tissue. The interface, can be placed in a thermoregulated chamber and connected to the electronic module by an extension (not shown).

C. a computer which has an acquisition card allowing both the digitalization of the analogic signals and the stimulation and finally, a software which allows the electrophysiological responses to be analyzed.

Figure 2:
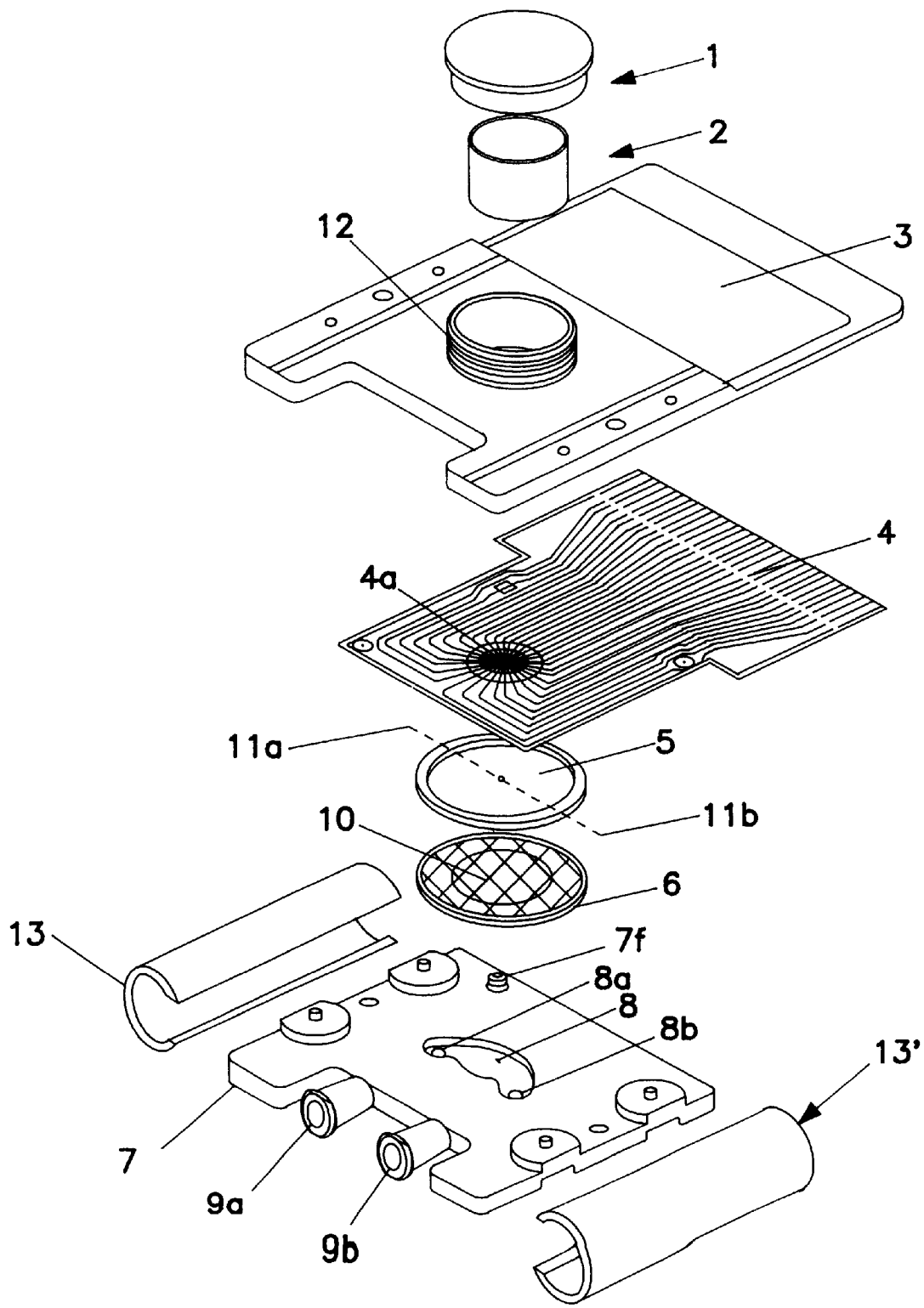
FIG. 2 is an exploded view of the apparatus of the invention.

The schematic diagram of the biological/electronic interface is represented in FIG. 2.

In a preferred implementation, represented in the FIG. 2, the device according to the invention can be defined in the following manner: it comprises two half-cards, the lower one (7) and the upper one (3) which fit together to form the operational arrangement.

The lower half-card has a cavity (8) which contains the liquid culture medium, comprising two supply pipes (8a) and (8b), each forming at its end a lock system (9a) and (9b). The cavity is surmounted by a transparent and permeable membrane (6) on which the tissue sample rests (10). A seal (5) provides water-tighness when the two half-cards (7) and (3) are fitted together. The seal can support one or more microdialysis probes (11A) and (11B) the details of which are provided in FIG. 3.

The upper half-card comprises an outlying well (12) inside which, a sleeve (2) slides. The sleeve can be lowered when the cap (1) is screwed down.

The two half-cards fit into each other and are fixed together by clips (13) and (13'). The lowering of the sleeve (2) by progressively pressing on the flexible printed circuit (see detail FIG. 4 and 5) (4), moves the gold-plated electrodes (4a) (tags upwards) downwards, which can thus touch the surface of the tissular explant (10). According to the texture of the tissue, a sufficient pressure at the level of the printed circuit (4) will allow the electrodes (4a) to penetrate inside the explant (10), if necessary.

The membrane of the interface can be characterized in the following manner:

the various tests carried out indicate that cultures can survive on membrane whose pore can vary from 0.02 to 10 $\mu$m. The chemical composidion of the membrane does not seem to be a determining factor. Membranes of Millicell CM (Millipore), Anopore (Whatman), polycarbonate, PET types give equivalent results.

Characteristics of the flexible printed circuit:

Design: 16 steps circuit=76 mm

Materials: Upilex 50 μm+Ci ED 35 μm+Au 0.8 μm

Execution: circuit supplied on a film of 69.975 μm width with S 70 perforation

Tolerances:
  thickness Au 0.2/0.3 μm
  width±75 μm
  image s/perfo±65 μm
  width of the tracks in the window kapton±15 μm Length of flying leads (initially for the transfer automatic bonding technology) can vary from 1.5 to 3.5 mm.

Figure 3B:
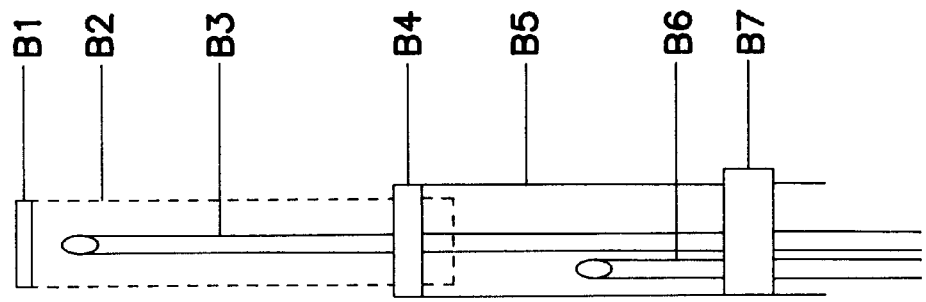
FIG. 3B is a cross section of a probe of the invention.
Figure 3A:
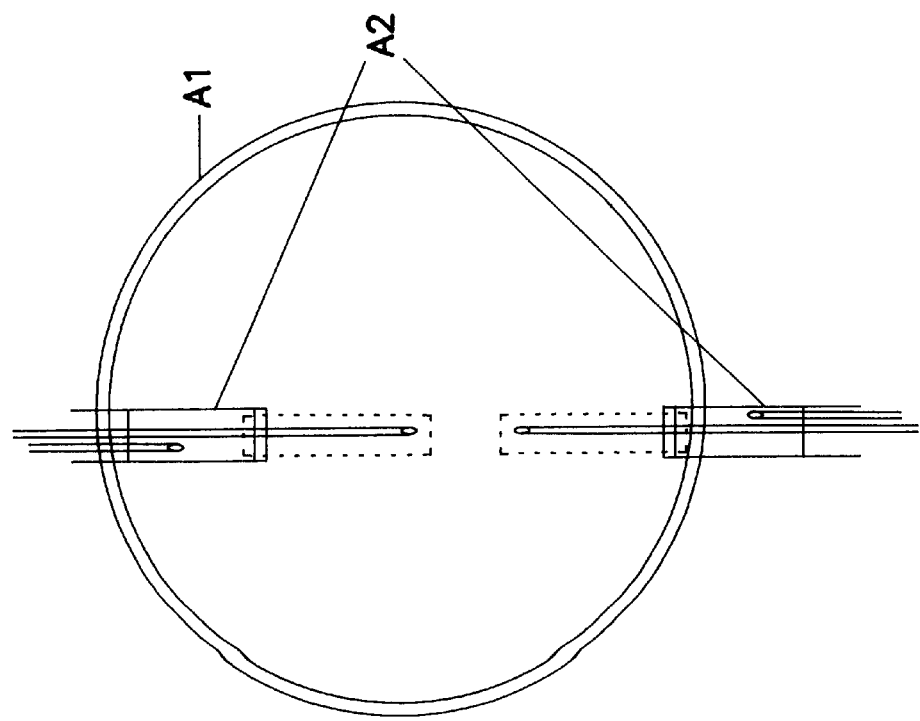
FIG. 3A is a cross section of the microdialysis device.

The schematic diagram of the microdialysis device is represented in FIG. 3.

One or more microdialysis probes (A2) pass through a silicon seal (A1). The detail of one probe is represented in FIG. 3B. A microdialysis bag with a 200 to 300 μm outer diameter (B2) is sealed at its end by a silicon or Epon resin (B1), then inserted into a tube (B5). The impermeability of the connection is produced by a drop of silicon glue (B4 and B7). The dialysis bag is perfused by means of two tubes made of fused, silica. The first tube (B3) penetrates as far as the end of the bag and supplies the perfusion solution. The second tube (B6) recovers the dialyzate. The probes are perfused by a physiological solution delivered by means of an automatic syringe-driver. The flow rate of the perfusion is generally comprised between 0.1 and 2 μl/min. The probes can be placed either on the surface of the culture, or be sandwiched between two slices of tissue. The dialysate is directly injected into a pump for HPLC via an electrical 6-port valve with 6 channels, or also can be recovered into flasks ad hoc for subsequent injections.

Figure 4:
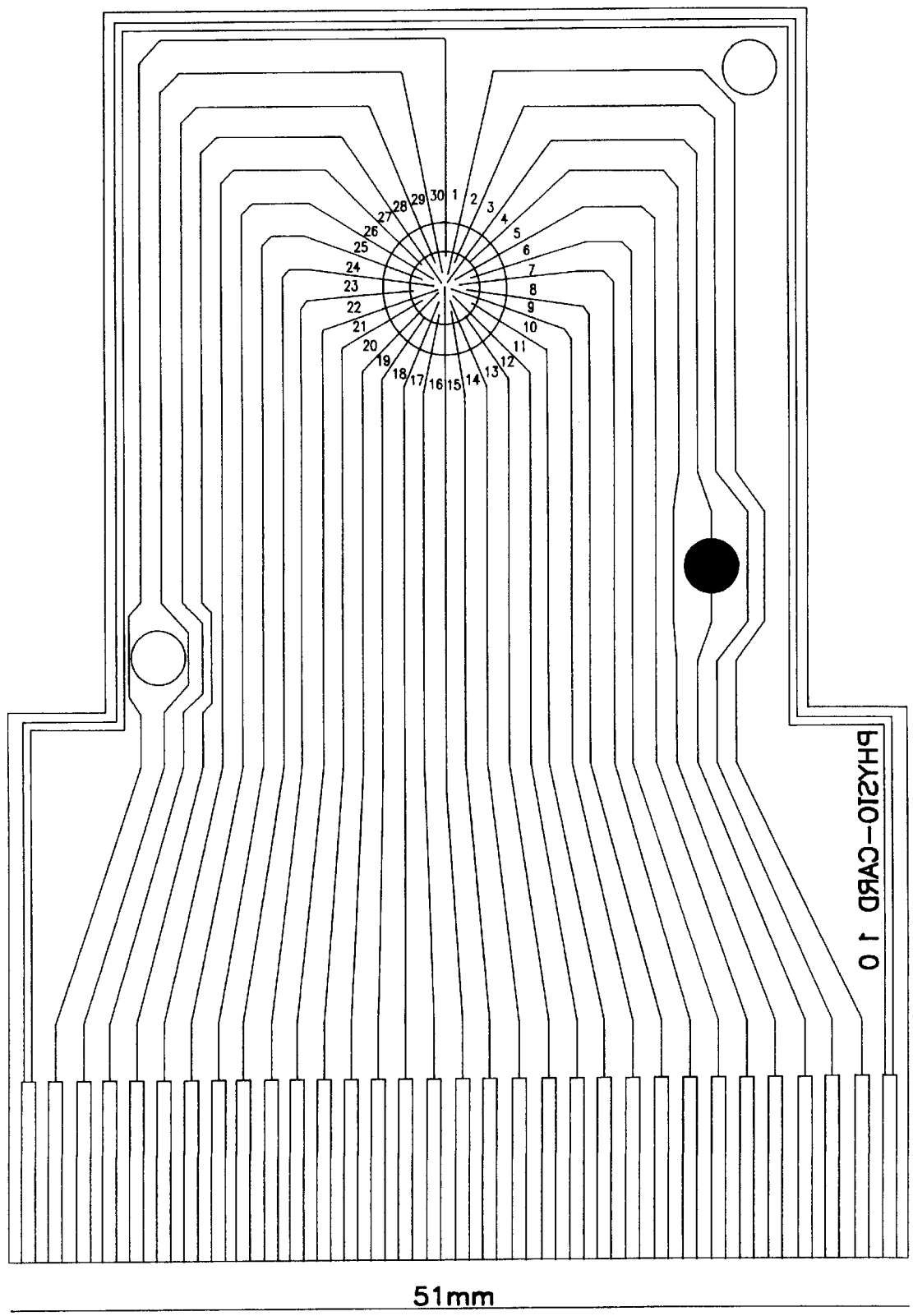
FIGS. 4 and 5 are plan views of the printed circuit.
Figure 5:
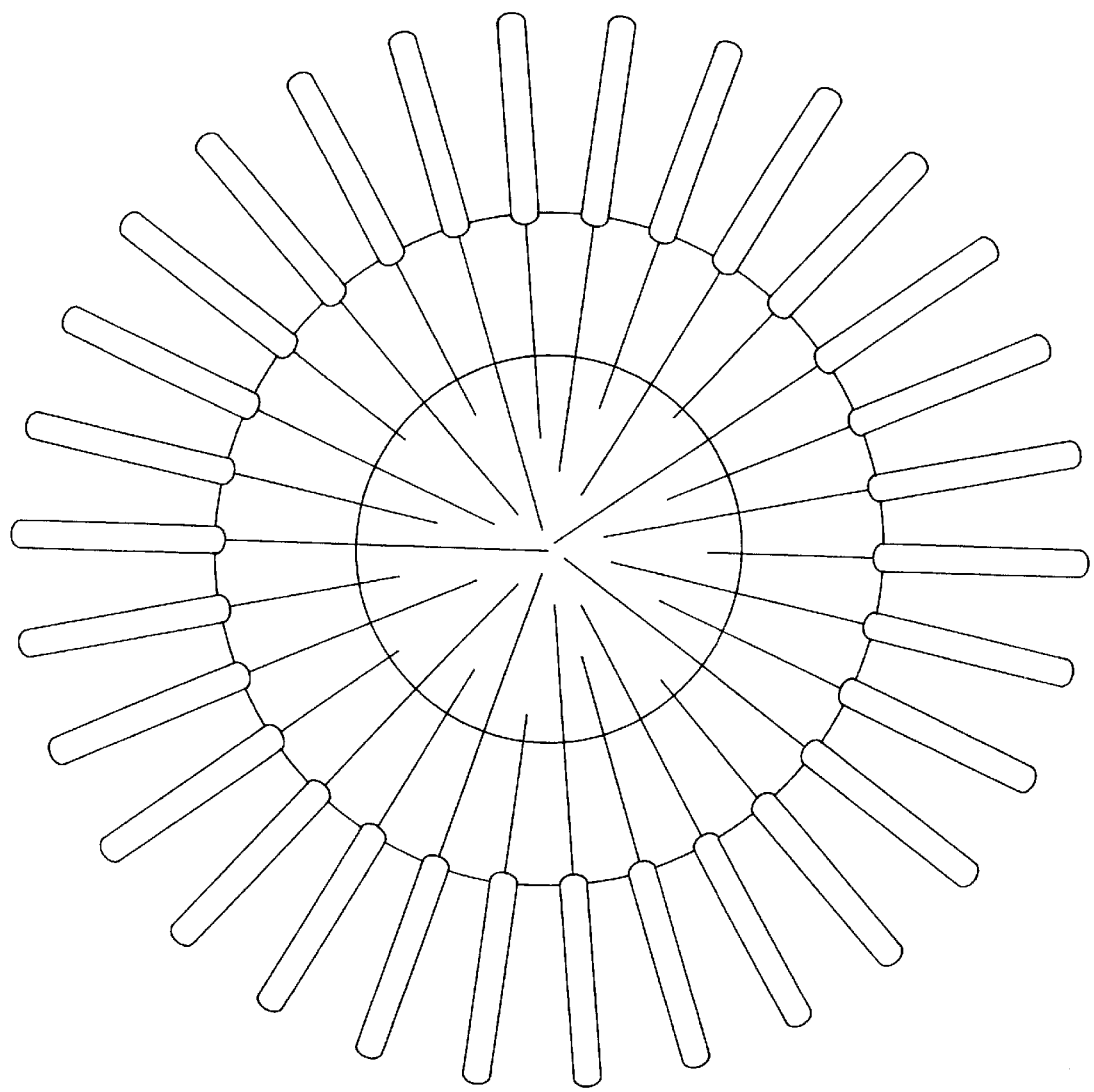

FIG. 4 and 5: details of the printed circuit.

Figure 6:
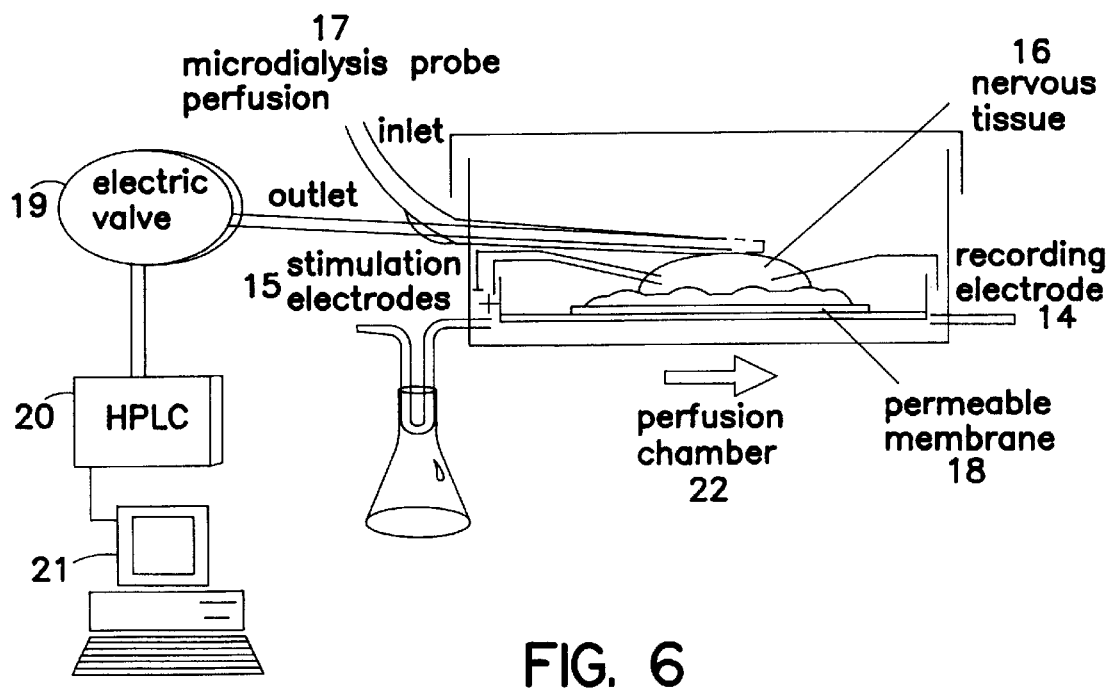
FIG. 6 is a schematic illustration of the system for simultaneous recording of electrphysiological activity and biochemical analysis.
Figure 7B:
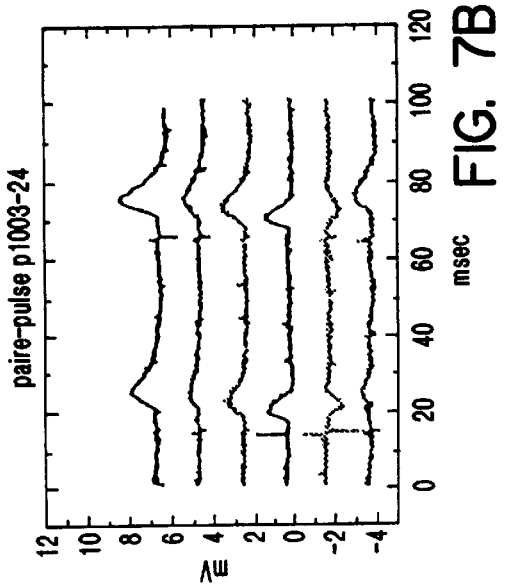
FIGS. 7A to D are graphs of responses after a series of pair-pulse stimulation paradigm.
Figure 7D:
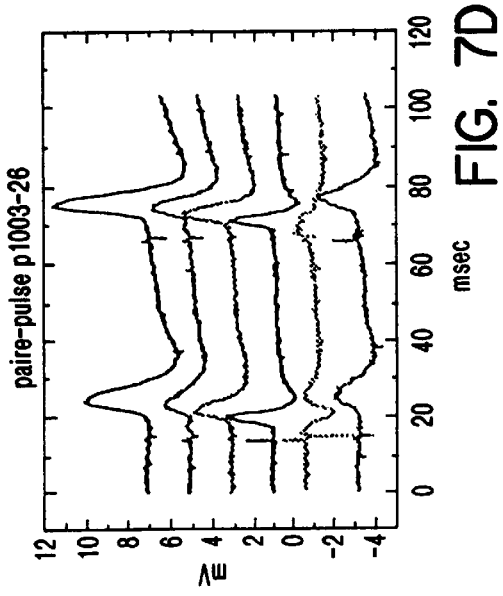
Figure 7A:
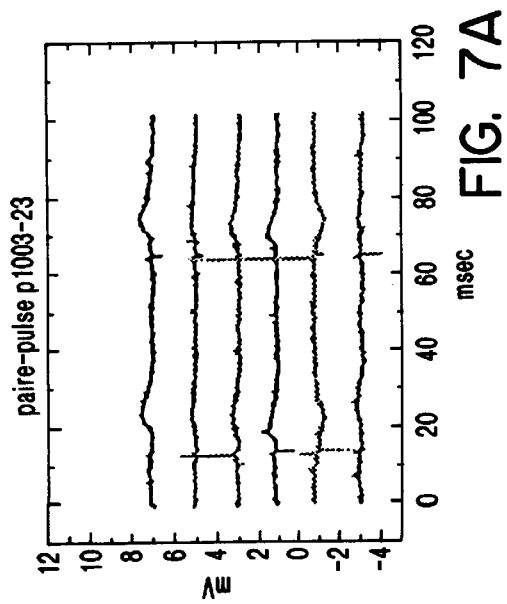
Figure 7C:
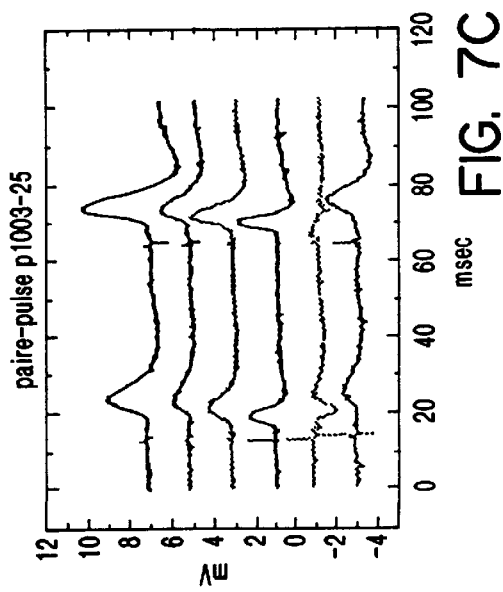
Figure 8A:
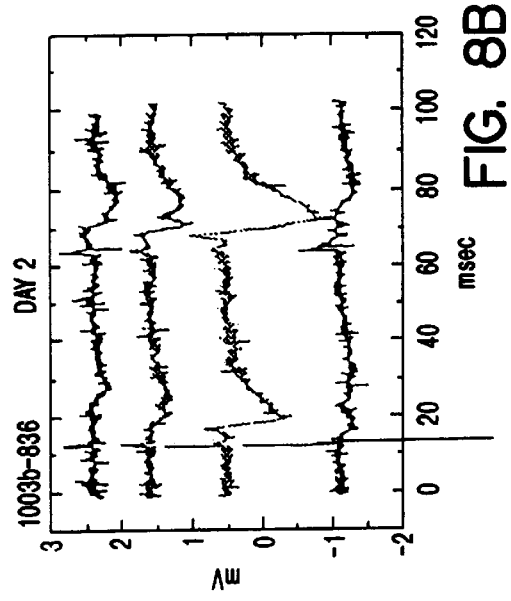
FIGS. 8A to D are graphs of responses obtained after four days of continuous stimulation.
Figure 8B:
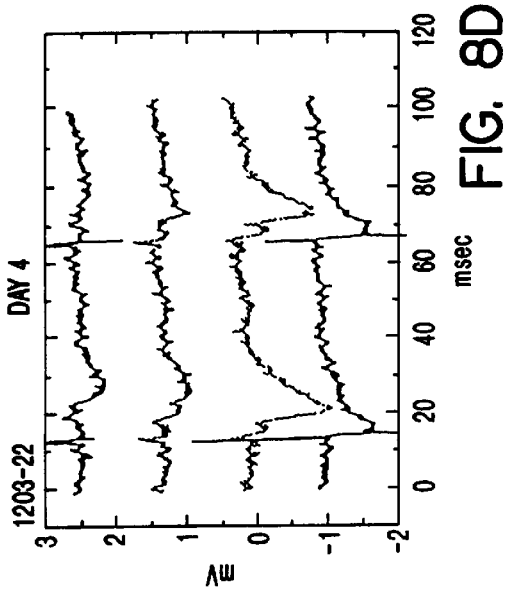
Figure 8C:
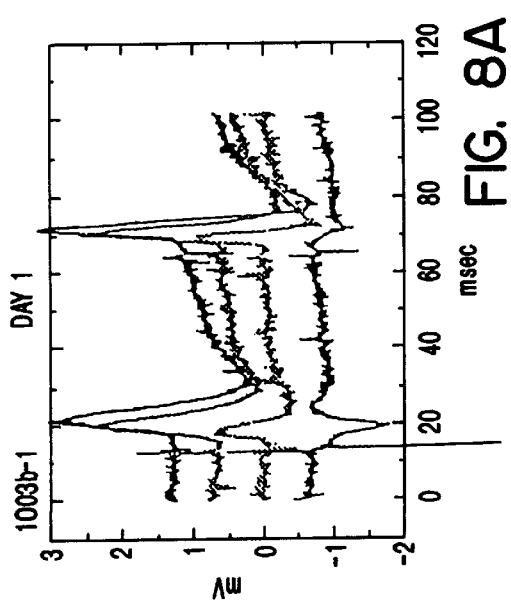
Figure 8D:
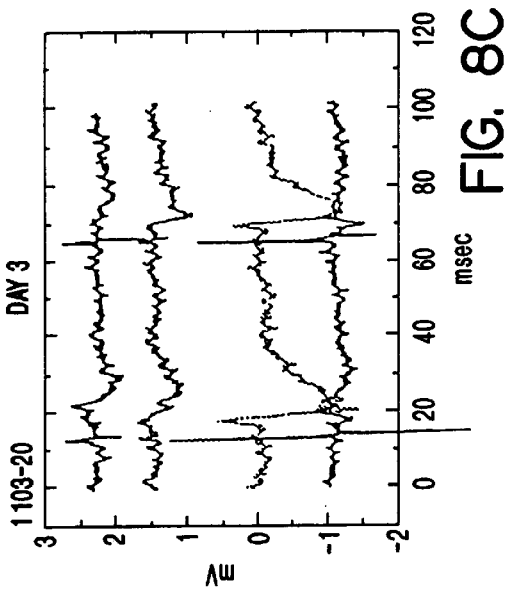

FIG. 6 is a schematic illustration of the system which allows simultaneous recording of electrophysiological activity and biochemical analysis of the microdialysate by an HPLC apparatus (seen in transversal section). Pulses of stimulation can be delivered through stimulating electrodes (15) to the nervous tissue (16) and consecutive evoked responses are recorded by one or several electrodes (14). In addition, molecules released by the tissue or coming from the perfusion chamber (22) through the permeable membrane (18) can be collected by a microdialysis probe (17). Outlet microdialyzates are injected in an HPLC (20) device by an electric valve (19). Chromatographic analyses are performed by a dedicated computer software (21).

FIG. 7 represents examples of evoked responses obtained after a series of pair-pulse stimulation paradigm. Six simultaneous recordings were performed in different hippocampus CA3 and CA1 areas of an organotypic slice culture. Stimulations were applied in the CA3 region.

FIG. 8 shows examples of evoked responses obtained after several days of continuous stimulations (one pair-pulse stimulation every minute). FIG. 8A represents an example of responses recorded during the first day, in FIGS. 8B, 8C and 8D, responses recorded in the following days.

FIG. 9 shows an example of one experiment of simultaneous recording of electrophysiological activity (A,C,E,G,I) and biochemical analysis (B,D,F,H,J) of dopamine diffusion through an hippocampal slice culture, HPLC chromotographs are represented in the left column while concomitant evoked neural activities are illustrated in the right column.

Similarly other mediators can be registered in the same manner such as acetylcholine, noradrenaline, adrenaline and serotonine using similar modes of detection.

Figure 10:
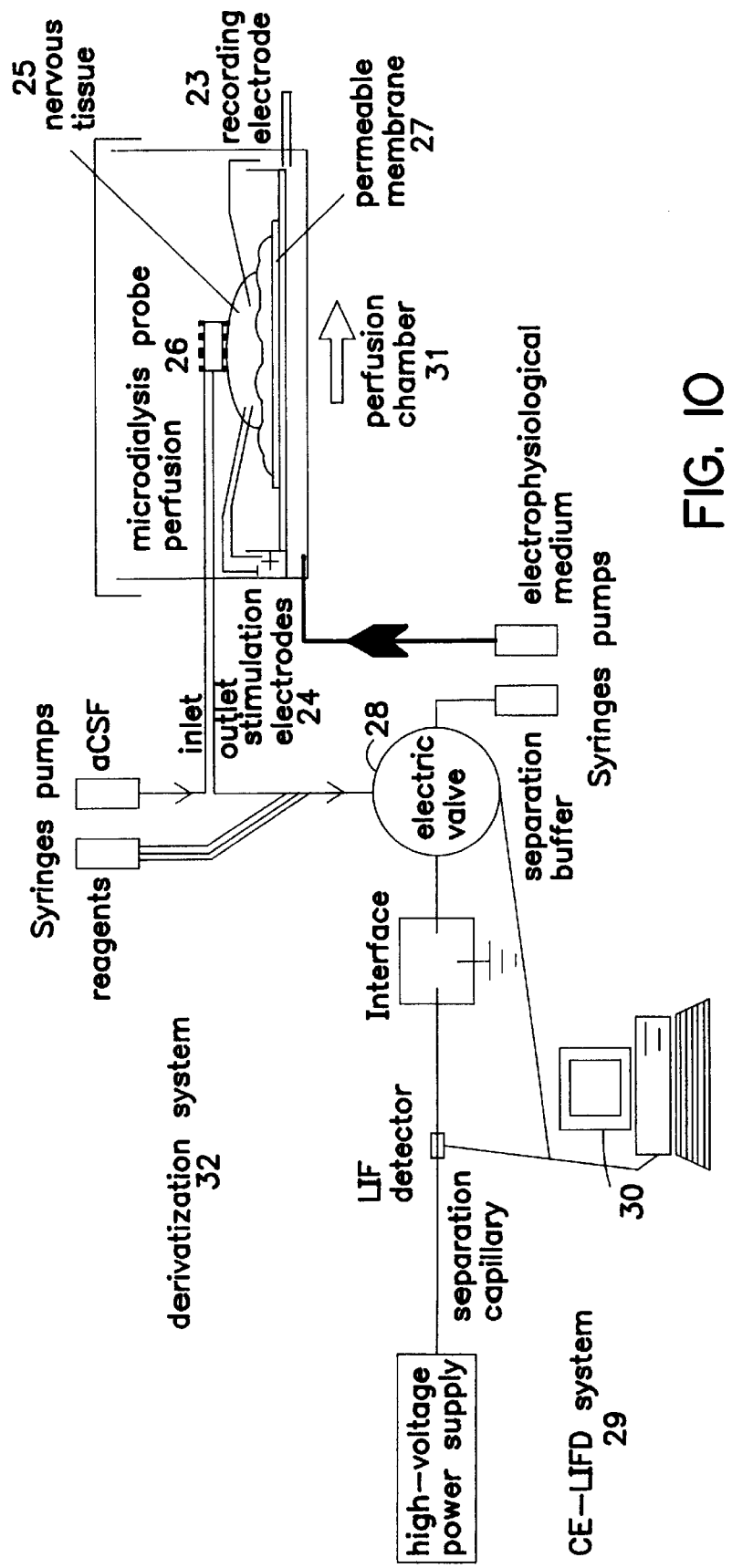
FIG. 10 is a schematic illustration of a system for simultaneous recording of electrophysiological activity and biochemical analysis using a capillary electrophoresis apparatus.

FIG. 10 represents a schematic illustration of the system (seen in transversal section) which allows the simultaneous recording of the electrophysiological activity and the biochemical analysis of the microdialysate using a capillary electrophoresis apparatus. Pulses of stimulation can be delivered through stimulating electrodes (24) to the nervous tissue (25) and consecutive evoked responses recorded by one or several electrodes (23). In addition, molecules released by the tissue or coming from the perfusion chamber (31) through the permeable membrane (27) can be collected by a microdialysis probe (26). Outlet microdialysates are injected in a capillary electrophoresis device (29') by an electric valve (28). Molecules present in the microdialysate are derivadzed (32) and capillary electrophoresis analyses are performed through a CE-LIFD system (29) by a dedicated computer software (30).

FIG. 11 shows as an example, an experiment of simultaneous recordings of electrophysiological activity and biochemical analysis of a microdialysate by capillary electrophoresis. A pattern of 100 stimulations was applied to the tissue, the first and the last responses are illustrated in FIG. 11A and B. FIG. 11C represents the recovery of electrophysiological response. Results of the time course release of glutamate present in the microdialysate are indicated in FIG. 11D after a stimulation of 3 Hz during 30 sec.

Figures 12A, 12B:
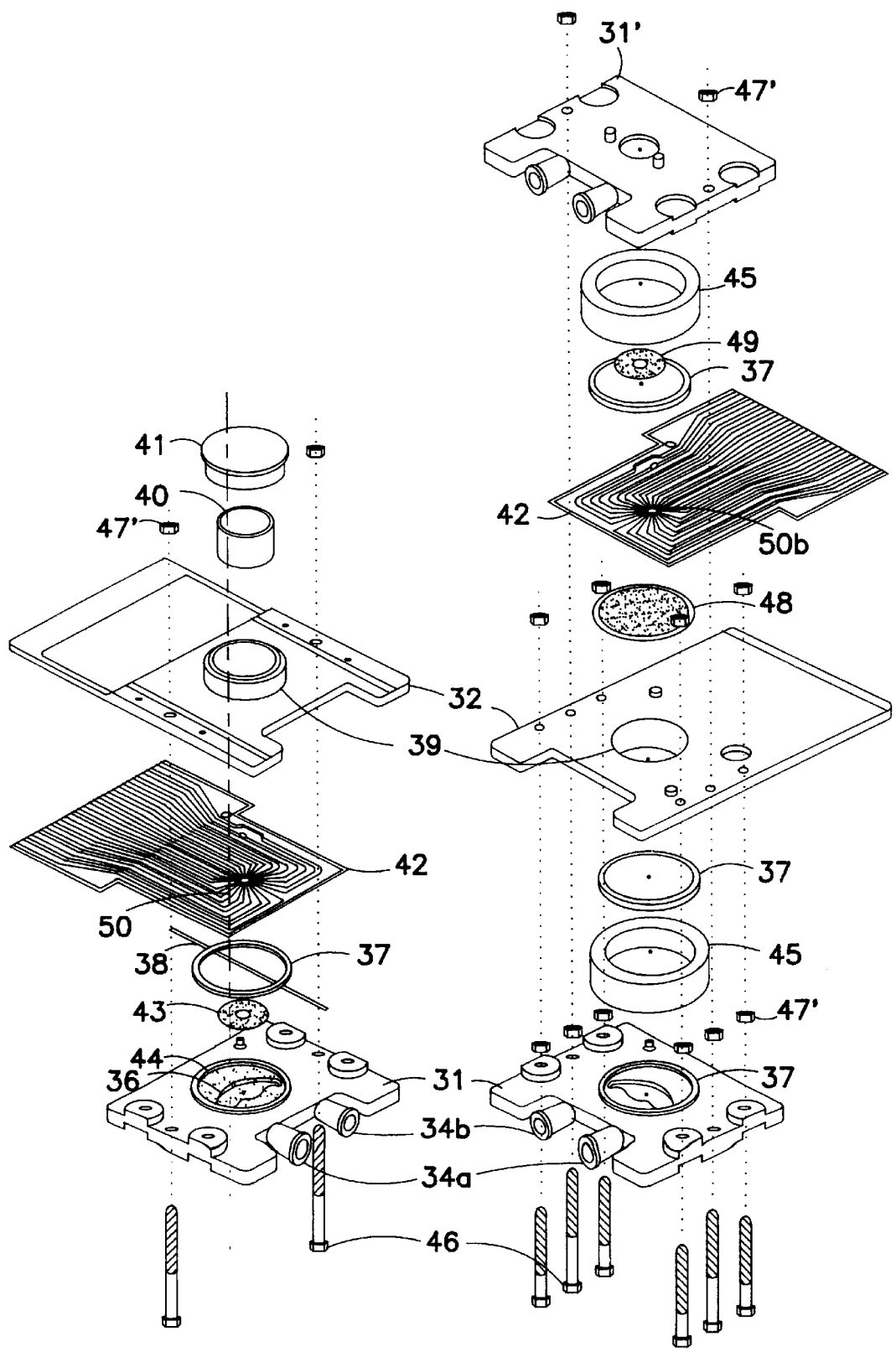
FIG. 12A is an outline of the biological/electronic interface for an upperside recording and FIG. 12B is the said interface for the underside recording.
Figure 13:
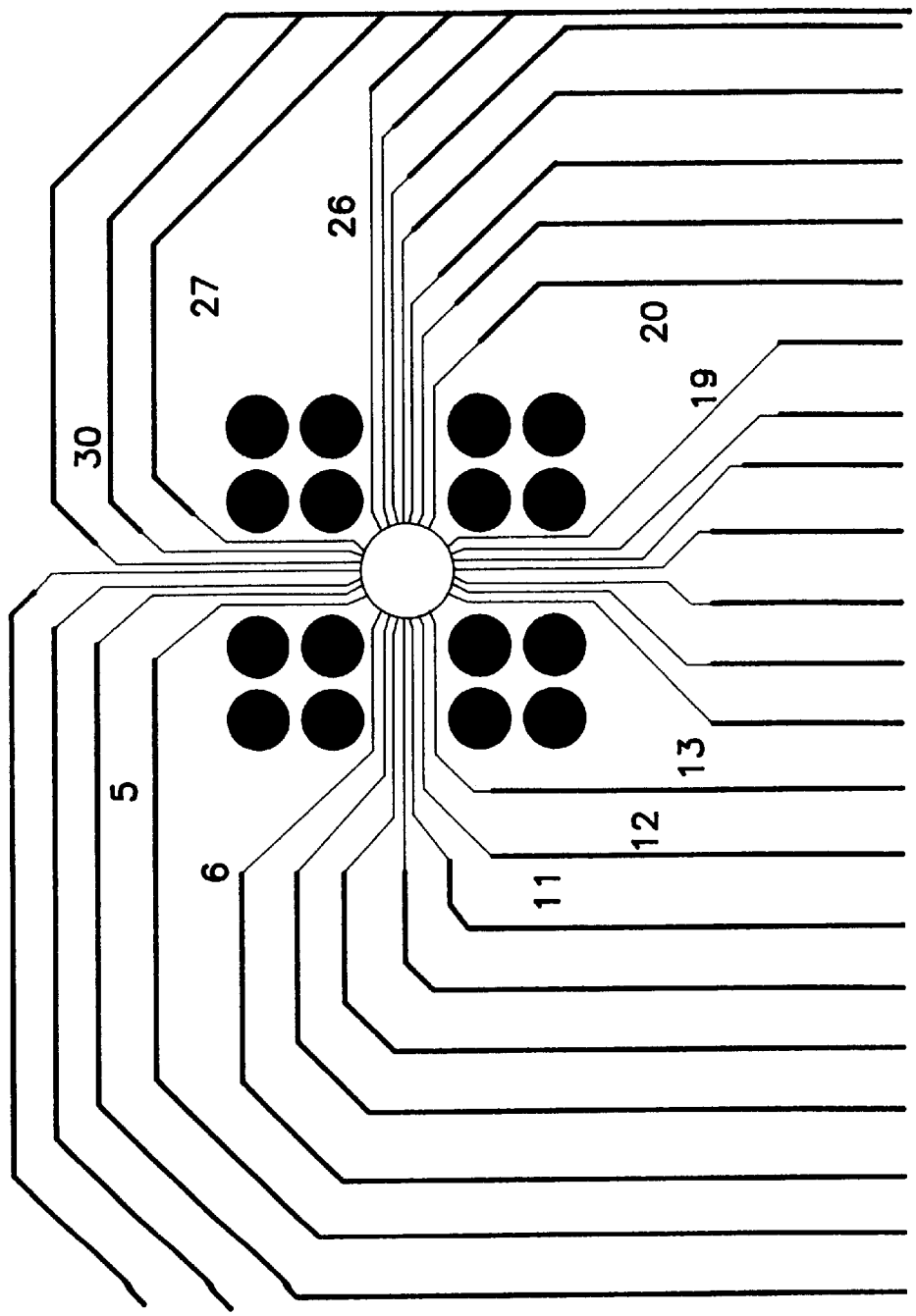
FIG. 13 is a magnified view of the recording network scheme.
Figure 14A:
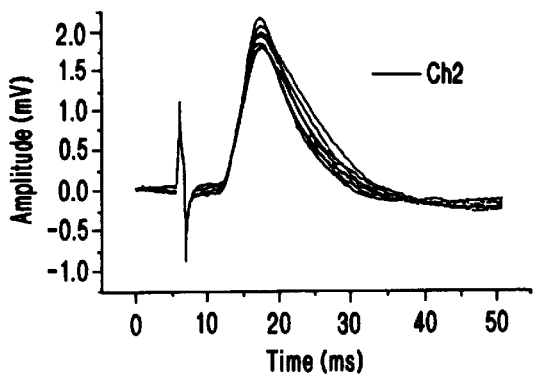
FIG. 14 illustrates sample recording conducted with rat hippocampus organotypic culture.
Figure 14B:
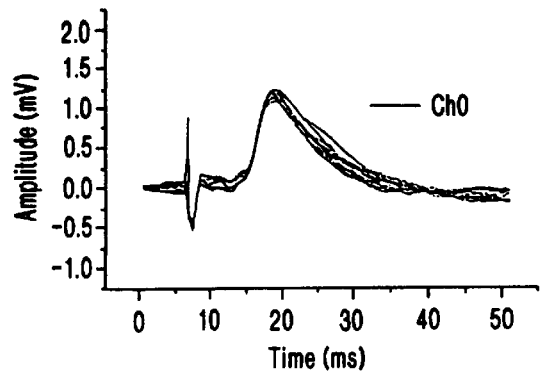
Figure 14C:
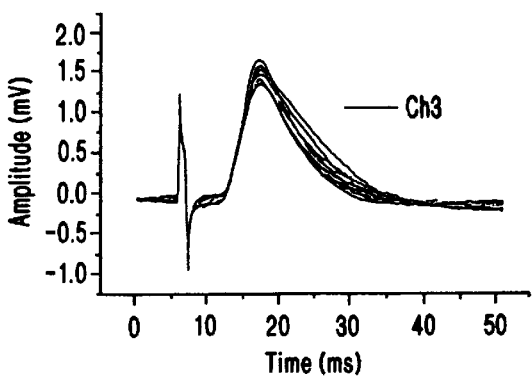
Figure 14D:
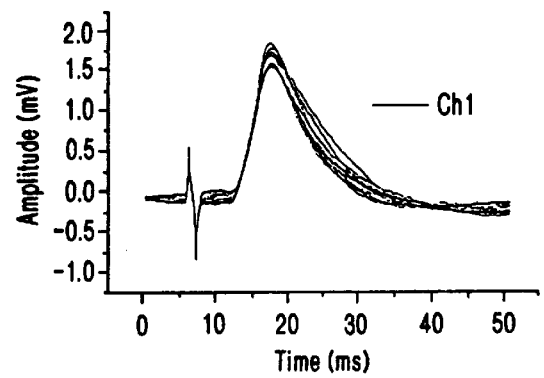
Figure 14E:
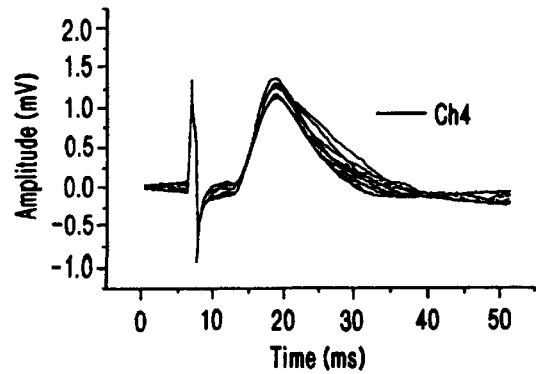

FIG. 12A gives an outline of the biological/electronic interface intended for upperside recording;

FIG. 12B shows a biological/electronic interface for underside recording;

FIG. 13 is a magnified view of the recording network scheme; and

FIG. 14 shows sample recordings conducted with a rat hippocampus organotypic culture.

In the preferred embodiment, represented on FIG. 12, the device is defined as follows: it comprises 2 half-cards for performing upperside recording (FIG. 12A), a lower (31) and an upper card (32) which once assembled together yield a functional set-up. The device includes 3 half-cards intended to carry out underside recording (FIG. 12B).

FIG. 12A

The lower half-card is provided with a cavity (33) which contains the liquid culture medium and with two admission tubings, each provided at the edge portion with a Luer system (34a) and (34b), that can accommodate a rubber screw cap. This cavity is covered with a transparent permeable membrane (35) on which the isolated tissue is disposed (36). A gasket (37) ensures tight closure when the two half-cards (31) and (32), are assembled. The gasket (37) can accommodate one or a number of microdialysis probes (38). The upper half-card (32) includes an off-center well (39) with a sliding socket inside (40). The socket (40) can be driven downward by tightening the screw cap (41). The two half-cards fit together and are connected by means of screws (46') and nuts (47'). The downward movement of the socket (40) will drive down the gold-plated electrodes (50) as it gradually presses on the flexible printed circuit board (42). The electrodes (41) will then be brought into contact with the tissue explant surface (43).

FIG. 12B

The lower half-card has a cavity (44) containing the liquid culture medium, provided with two inlet/admission tubings, each one being equiped at the edge portion with a Luer system (34a) and (34b) whereby a rubber cap can be screwed on. A plastic ring (45) is screwed on top of the off-center well (39) of the upper half-card (32). This card is then inverted and laid on the lower half-card (31). The two half-cards are tightly connected by means of four screws (46) and four nuts (47) thus forming the lower assembly. Two gaskets (37) ensure tight closure of the infusion chamber thus obtained.

The off-center well (39) is covered by a permeable transparent membrane (48) on top of which is laid the flexible printed circuit board (42). A Teflon® eyelet bearing the isolated tissue or culture (49) may then be disposed on the circuit fixed-end electrodes (50b). A gasket (37) and the plastic rin (45) ensure tight closure of the gas chamber formed by connecting the half-card (31) by means of two screws (46) and two nuts (47) to the lower assembly comprised of the two half-cards (32) and (31).

FIG. 13

This is a magnified vue of the recording network scheme. This network is made up of 30 recording electrodes and 17 bored holes so that the culture medium flowing accross the membrane by capillarity can form a thin liquid cover film on the tissue. The central hole measures 1,5 mm in diameter.

FIG. 14

Sample recordings derived from a rat hippocampus organotypic culture are shown, namely sample electrophysiological responses elicited by a series of 15 stimulations between two network electrodes located at $CA_3$. The 15 recording plots derived from each of the 5 recording electrodes located at $CA_1$ are vertically aligned.

Chemical composition of the different culture media:

|  | 100 ml | 200 ml |
|---|---|---|
| MEM 2x | 25 ml | 50 ml |
| Tris 5 mM | 60 mg | 120 mg |
| Penstrep | 1 ml | 2 ml |
| NaHCO$_3$ | 460 µl | 910 µl |
| Sterile H$_2$O | to 50 ml | to 100 ml |
| Horse serum | 25 ml | 50 ml |
| Hank's medium | 25 ml | 50 ml |

DISSECTION MEDIUM (medium for culturing):

| MEM 2x | 50 ml |
|---|---|
| Penstrep | 1 ml |
| Tris 10 mM | 120 mg |
| Sterile H$_2$O | (completed to 100 ml) |

DMEM 10% FCS (medium for dissociated cells):

| DMEM 2x | 45 ml |
|---|---|
| NaHCO$_3$ | 1.5 ml |
| Penstrep | 1 ml |
| Sterile H$_2$O | (completed to 90 ml) |
| FCS | 10 ml |

ODM MEDIUM (medium defined without serum)

| Complementary medium | | |
|---|---|---|
| pH | 7.26 | |
| Osm | 291 mosm/kg | |
| CaCl$_2$ | 1 mM | 22 mg |
| KCl | 3 mM | 22.2 mg |
| NaCl | 0.8 % | 800 mg |
| MgSO$_4$ | 2 mM | 49 mg |
| (VITC) | 4 mM | 70 mg |
| Glucose | 0.6 mM | 100 mg |
| HEPES | 25 mM | 595 mg |
| Tris | 10 mM | 120 mg |
| NaHCO$_3$ | 4.2 mM | 34.5 mg |
| KH$_2$PO$_4$ | 1.25 mM | 17 mg |
| ↓ | | |
| 100 ml H$_2$O | | |
| MEM medium 1x | | |
| MEM 2x | 25 ml | |
| Tris | 60 mg | |
| NaHCO$_3$ | 460 µl of 7.5% stock solution | |
| Penstrep | 1 ml | |
| ↓ | | |
| 25 ml H$_2$O | the total made 50 ml | |
| ODM medium | | |
| MEM medium 1x | 50 ml | |
| Complementary medium | 50 ml | |
| ↓ | | |
| Filter | | |
| pH | 7.32 (before incubation) | |
| pH | 7.1 (after incubation) | |
| Osm | 307 mosm/kg | |

What is claimed is:

1. In an improved device for studying and recording electrophysiological phenomena in a culture of excitable tissues wherein the tissue is laid flat on a network of electrodes comprising a lower card with a perfusion medium in a perfusion chamber sealed by a permeable and transparent membrane and an upper card and a lower card with a flexible printed circuit bearing a network of electrode, the improvement comprising the two lower cards and the upper card which when assembled together for recording yield a functional set up.

2. The device of claim 1 wherein the lower card is provided with a cavity which contains liquid culture medium and has two admission tubings ended with a plugging system, the said cavity being covered with a transparent permeable membrane on which tissues are disposed.

3. The device of claim 1 in which the cards are assembled by a gasket which ensures tight closure.

4. The device of claim 1 in which the upper card includes an off-center well with a sliding socket inside.

5. The device of claim 1 wherein the cards fit together and are assembled by means of screws and nuts.

6. The device of claim 1 wherein there is an off center including a sliding socket, the off center being covered by a permeable membrane on the top of which is laid the flexible printed circuit board bearing a network electrodes.

7. A method comprising simultaneous measuring and recording electrophysiologicals of excitable cells using an improved device of claim 1.

* * * * *